United States Patent
Tamura et al.

[11] 3,953,489
[45] Apr. 27, 1976

[54] ALKYL 2-NITRO-5-(2,4-DICHLOROPHENOXY)-THIOBENZOATES

[75] Inventors: Saburo Tamura, Tokyo; Tetsuo Takematsu, Utsunomiya; Hisae Haruta, Ibaraki, all of Japan

[73] Assignee: Fujisawa Pharmaceutical Co., Ltd., Osaka, Japan

[22] Filed: Jan. 17, 1975

[21] Appl. No.: 542,052

[30] Foreign Application Priority Data
Apr. 10, 1974 Japan.................................. 49-41129
June 10, 1974 Japan.................................. 49-66276

[52] U.S. Cl............................. 260/455 R; 71/100
[51] Int. Cl.²........................................ C07C 153/07
[58] Field of Search.................... 260/455 R; 71/100

[56] References Cited
UNITED STATES PATENTS
3,333,945  8/1967  Richter et al................... 260/455 R
3,784,635  1/1974  Theissen.......................... 260/455 R
3,867,543  2/1975  Kohn................................ 260/455 R OTHER PUBLICATIONS
Houben–Weyl, Meth. Der. Org. Chem. (1955), pp. 753–756.
J. Org. Chem. (U.S.S.R.), pp. 1102–1105 (1959).

Primary Examiner—Elbert L. Roberts
Assistant Examiner—D. R. Phillips
Attorney, Agent, or Firm—Bierman & Bierman

[57] ABSTRACT

A compound of the formula

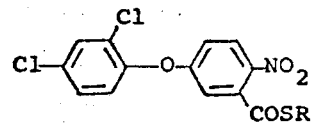

wherein R is a lower alkyl group, useful as a herbicide, and a method of its preparation. A method of killing weeds using said compound is also disclosed.

5 Claims, 3 Drawing Figures

Degree of injury of Compound No. 1 of the present invention {methyl 2-nitro-5-(2',4'-dichlorophenoxy) thiobenzoate} to plants

FIG. 3

Figure 1:
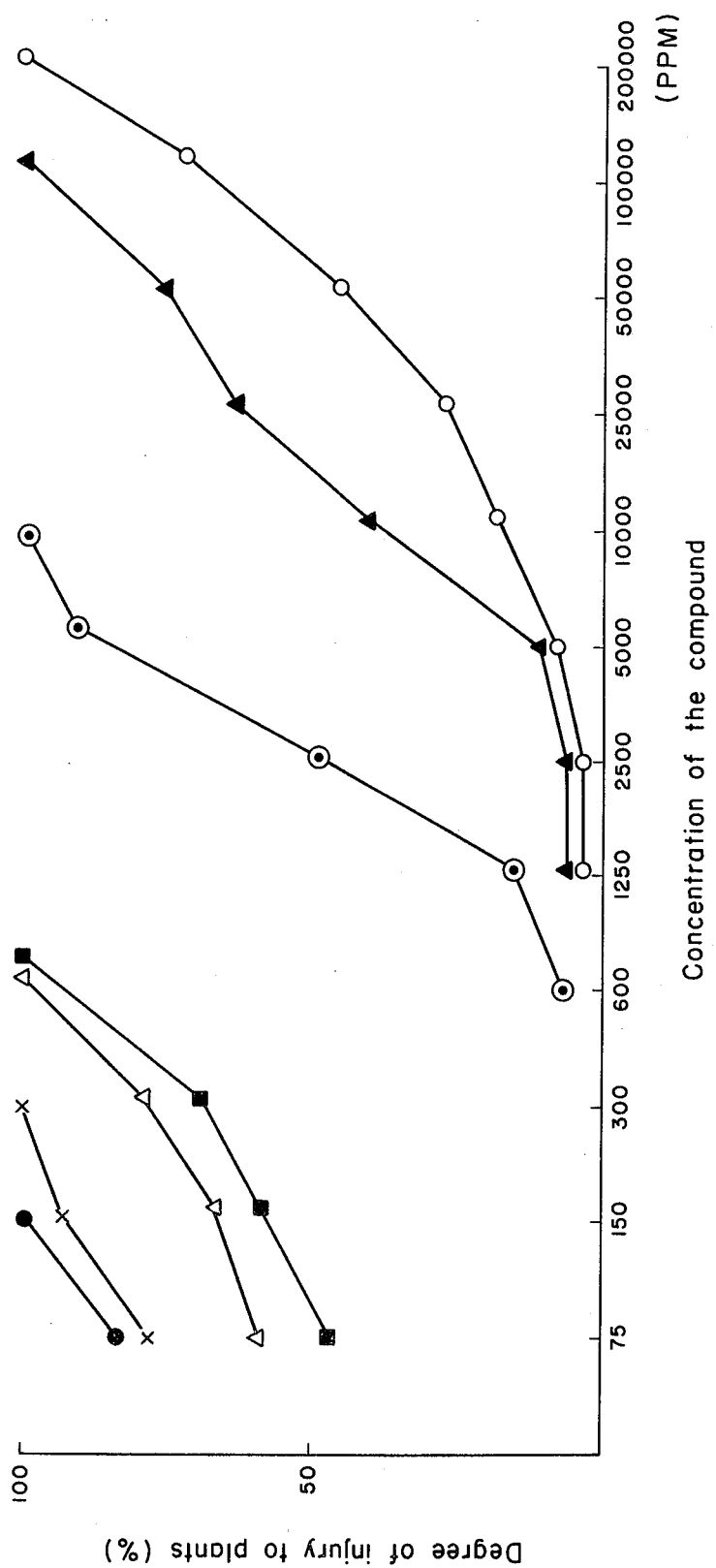
Figure 2:
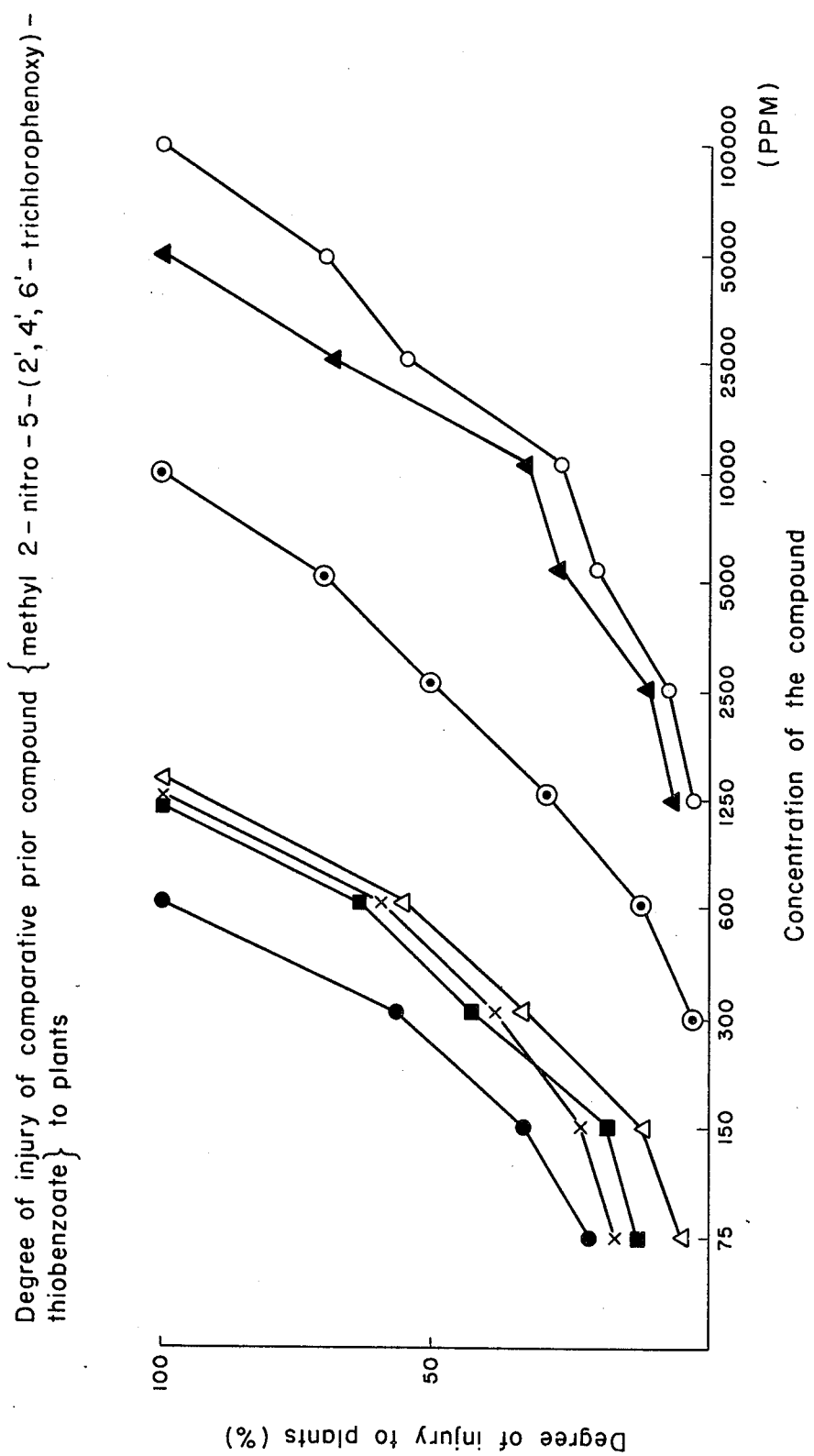

Legend for Figs. 1 and 2

○——○ Wheat (Triticum aestivum L.)

●——● Wild radish (Raphanus raphanistrum L.)

△——△ Smallflower galinsoga (Galinsoga parviflora Cav)

▲——▲ Rice (Oryza sativa L.)

■——■ Speedwell (Veronica didyma Tenore var. lilacina Yamazaki)

⊙——⊙ Corn (Zea mays L.)

×——× Kidney bean (Phaseolus vulgaris L.)

ALKYL 2-NITRO-5-(2,4-DICHLOROPHENOXY)-THIOBENZOATES

The present invention relates to substituted a phenoxythiobenzoic acid ester, a process for preparation thereof and its use as herbicide. More particularly, it relates to alkyl2-nitro-5-(2',4'-dichlorophenoxy)thiobenzoate, a process for preparation thereof and methods and compositions for killing weeds, especially in wheat fields.

Heretofore, with regard to substituted phenoxythiobenzoic acid esters, only methyl 2-nitro-5-(2',4',6'-trichlorophenoxy)thiobenzoate has been specifically known to be used as a herbicide (hereinafter referred to as "prior compound". cf. U.S. Pat. No. 3,784,635.) However said prior compound has never shown sufficient herbicidal activity against weeds coupled with no injury to the cultivated plant, especially wheat.

The present invention is based on the observation that alkyl 2-nitro-5-(2',4'-dichlorophenoxy)thiobenzoate (hereinafter referred to "compound of the invention"), has higher herbicidal activities against weeds and does less injury to cultivated plants, especially in the treatment of wheat fields in comparison with the prior compound.

Accordingly, the object of the invention is to provide as a new compound alkyl 2-nitro-5-(2',4'-dichlorophenoxy)thiobenzoate.

Another object of the invention is to provide a process for preparing the compound of the invention.

Another important object of the invention is to provide compositions for killing weeds comprising the compound of the invention which have considerably more herbicidal effectiveness against weeds, less injurious to the culivated plant, are safer and more economical to use than the prior compound.

The compound of the invention is new and shown by the following general formula:

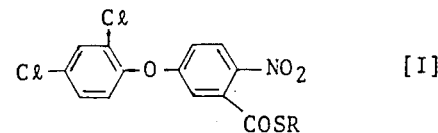

(wherein R is lower alkyl)

R is, for example, an alkyl radical of 1 to 3 carbon atoms, i.e. methyl, ethyl, n-propyl or isopropyl.

Preferred compounds of the invention are as follows.

| Compound No. | Formula |
|---|---|
| 1 | Cl-C6H3(Cl)-O-C6H3(NO2)-COSCH3 |
| 2 | Cl-C6H3(Cl)-O-C6H3(NO2)-COSCH2CH3 |
| 3 | Cl-C6H3(Cl)-O-C6H3(NO2)-COSCH2CH2CH3 |
| 4 | Cl-C6H3(Cl)-O-C6H3(NO2)-COSCH(CH3)2 |

The compound of the invention [I] can be prepared by reacting a compound of the formula:

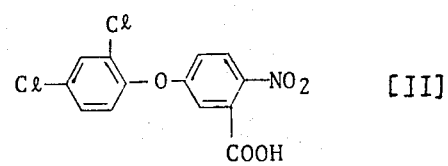

or its reactive derivative at the carboxy group with a reagent of the formula:

R — SH  [III]

wherein R is lower alkyl group, or its salt.

A starting compound of the formula [II] to be used in this process is disclosed by U.S. Pat. No. 3,784,635.

As examples of the reactive derivative at the carboxy group of compound [II], there are mentioned acid halide, acid anhydride, acid amide, ester, etc. and preferably acid chloride, acid azide, mixed acid anhydride with aliphtic carboxylic acid, methyl ester, etc. These reactive derivatives can be used not only in the pure state but also in the crude state, for example, in a solution containing the reactive derivative which is activated at the carboxy group by reacting the compound [I], having carboxy group, with an activating agent such as thionyl chloride, etc.

The starting compound [II] having a carboxy group can be used in the form of the salt thereof, for example, salts with alkaline metals, alkaline earth metals, ammonia, or organic bases such as triethylamine, etc.

R of the reagent [III] stands for a lower alkyl group, such as an alkyl group of 1 to 3 carbon atoms, i.e. methyl, ethyl, n-propyl or isopropyl radical. As a salt of this reagent, there is mentioned, for example, the salt with a metal such as alkali metal, alkaline earth metal, etc.

The reaction of the present invention is usually conducted in a solvent. As examples of the solvents, there may be mentioned water, acetone, acetonitrile, chloroform, methylene chloride, tetrahydrofuran, ether, pyridine, dimethylsulfoxide, N,N-dimethylformamide, and hexamethylphosphoramide.

The reaction can be also conducted in the presence of a base such as alkali hydroxide, alkali bicarbonate, trialkylamine, pyridine, etc. If the base is liquid, it may serve as the solvent also.

The reaction temperature is not particularly limitative, but the reaction is usually conducted under cooling or at ambient temperature. The reaction product can be isolated and purified in a conventional manner.

Practical and preferred embodiments for the preparation of the compound of the invention are illustratively shown as follows.

EXAMPLE

After a mixture of 2-nitro-5-(2',4'-dichlorophenoxy)benzoic acid (12 g.), thionyl chloride (12 g.) and absolute benzene (30 ml.) was refluxed for 1 hour, benzene and excess thionyl chloride were distilled off from the mixture under reduced pressure. The residue was dissolved in ether (80 ml.), and the solution was added dropwise to 20% aqueous solution of sodium methyl mercaptan (15 g.) under vigorous stirring. The reaction mixture was stirred for additional 1 hour at ambient temperature and then was extracted with ether. The extract was dried over anhydrous sodium sulfate and then concentrated under reduced pressure to give yellow oil. Isopropylether was added to the oil and then allowed to stand for 24 hours in a refrigerator to give 13 g. of methyl 2-nitro-5-(2',4'-dichlorophenoxy)thiobenzoate as faint yellow prisms. (compound 1). MP : 77.5° – 78.5°C.

Elemental analysis for $C_{14}H_9NO_4SCl_2$:

|  | C | H | N | S | Cl |
|---|---|---|---|---|---|
| Calculated : | 46.97 | 2.53 | 3.91 | 8.96 | 19.81 |
| Found : | 47.16 | 2.36 | 4.02 | 9.20 | 19.75 |

The following compounds were prepared in a similar manner to that described in the above preparation, ethyl 2-nitro-5-(2',4'-dichlorophenoxyl)thiobenzoate(-compound 2).

MP : 74°–75°C

Elemental analysis for $C_{15}H_{11}NO_4SCl_2$:

|  | C | H | N | S | Cl |
|---|---|---|---|---|---|
| Calculated : | 48.43 | 2.98 | 3.77 | 8.62 | 19.06 |
| Found : | 48.56 | 2.71 | 3.48 | 8.57 | 19.14 | n-propyl 2-nitro-5-(2',4'-dichlorophenoxy)thiobenzoate (compound 3)

Elemental analysis for $C_{16}H_{13}NO_4SCl_2$:

|  | C | H | N | S | Cl |
|---|---|---|---|---|---|
| Calculated : | 49.78 | 3.39 | 3.63 | 8.31 | 18.37 |
| Found : | 49.68 | 3.54 | 3.44 | 8.60 | 18.46 | isopropyl 2-nitro-5-(2',4'-dichlorophenoxy)thiobenzoate (compound 4)

BP : 145°–150°C/1.2 mmHg

Elemental analysis for $C_{16}H_{13}NO_4SCl_2$:

|  | C | H | N | S | Cl |
|---|---|---|---|---|---|
| Calculated : | 49.78 | 3.39 | 3.63 | 8.31 | 18.37 |
| Found : | 49.52 | 3.49 | 3.64 | 8.52 | 18.15 |

The compound of the invention has extremely strong herbicidal activities. That is, the compound of the invention has superior herbicidal activity, even when used in small amounts, on the one hand and does little injury to the cultivated plants, (especially (Graminaceal) by its application thereto even in relatively large amounts on the other hand. Also, the compound of the invention can be applied in the treatment of stems and leaves as well as soil and submerged water soil without injury to the cultivated plant. Accordingly, it is to be understood that the compound of the invention is characterized in that it has a wide effective range between the effective concentration against weeds and the concentration at which the cultivated plant is injured. This means that the compound of the invention can be safely applied to cultivated plants. Further, the compound of the invention is characterized by having selective herbicidal activity among the family of the cultivated plant, especially Graminaceae. That is, the compound of the invention does little injury to rice (Oryza), corn (Sorghum), wheat (Triticum), barley (Hordeum) and rye (Secale), etc; (especially wheat) on the one hand and does barnyard grass (Echinochloa) on the other hand. Especially, it is to be noted that the compound of the invention can demonstrate very effectively its herbicidal activities in a wheat field. Incidentally, the compound of the invention is economical due to the fact it acts on the weeds even in low concentration.

The compounds of the present invention are effective against, for example, Compositae (e.g. annal fleabane, philadelphia fleabane, smallflower galinsoga and the like.), Polygonaceae (e.g. ladysthumb, dock and the like.) Scrophulariaceae (e.g. speedwell and the like.), Rubiaceae (e.g. catchweed bedstraw and the like.), Cruciferae (e.g. shepherdspurse and the like.), Boraginaceae (e.g. Kiurigusa [Japanese name] and the like.) and Chenopodiaceae (e.g. common lambsquarters and the like.), perennial weeds in a paddy field such as needle spikerush, arrowhead, etc. and aquatic floating weeds such as duckweed, greater-duckweed, etc.

Ranges of effective concentration of the compound of the invention depend not only on the kind of weeds but also on the kind and physiological ages of the cultivated plants. Thus, the concentration to be applied should be determined depending on the type of weeds to be treated and the period of application. Usually the effective concentration of the compound of the invention is preferably within the range of 0.5 – 5.0 g. per are.

The compound of the invention is used in the form of compositions comprising at least one compound of the invention as an active ingredient in association with an inert carrier and/or a conventional surface-active agent, and the said composition can be used as dusts, granules, tablets, wettable powder, emulsions, etc. In the compositions, the carriers may be solid, liquid or a combination thereof. Suitable carriers, are, for example, talc, bentonite, kaolin, diatomaceous earth, pyrophyllite, kaolinite, silicagel, calcium bicarbonate, starch, gum arabic, water, methanol, ethanol, acetone, benzene, etc. Further, auxiliary agent such as spreader, emulsifiers, etc., which are generally used in the preparation of agricultural chemicals, can be used as the occasion demands.

The application methods of the prepared herbicidal composition comprising the compound of the invention can vary depending on the purpose of usage and on the kind of plants to be treated. It is preferable to spray it onto the stems and leaves of weeds or to carry out soil treatment or submerged water treatment with it.

Additionally, said herbicidal composition can be also used singly or in the combination with any other herbicides, fungicides, nematocides, or insecticides. It is also possible to use the said herbicidal composition jointly with a fertilizer or any other plant growth regulating agents.

Herbicidal testing of the compound of Compound No. 1 of the present invention and of the comparative prior compound showed the results set forth in FIGS. 1–2.

TEST 1 (FOLIAGE TREATMENT TEST)

Test Plant
| | |
|---|---|
| Rice | *Oryza sativa* L. |
| Wheat | *Triticum aestivum* L. |
| Wild radish | *Raphanus raphanistrum* L. |
| Smallflower galinsoga | *Galinsoga parviflora* Cav. |
| Dock | *Rumex japonica* Houttuyn |
| Corn | *Zea mays* L. |
| Speedwell | *Veronica didyma* Tenore var. *lilacina* Yamazaki |
| Kidney bean | *Phaseolus vulgaris* L. |

All crop and weed seeds are surface seeded individually in clay pots packed with upland field soil and then sprinkled with screen soil in an amount sufficient to cover the seeds.

After germination of the seeds, an aqueous suspension of wettable powder containing test compound mentioned below with specified concentration and bentonite is sprayed onto the leaves at individually proper stages of seedling development which are as follows.

Wild radish: first true leaf
Kidney bean: first true leaf
Dock: first true leaf
Smallflower galinsoga: second true leaf
Speedwell: third true leaf
Rice: third true leaf
Wheat: third true leaf
Corn: third true leaf Eleven days after spraying, injury to growth of the individual plants is rated. The results are showed in FIGS. 1 – 2 and the selective herbicidal coefficients calculated on the basis of data obtained are given in the following table.

Table 1

| Test Compound | A | B | B/A | Index | A' | B | B/A' | Index | B' | B'/A' | Index |
|---|---|---|---|---|---|---|---|---|---|---|---|
| Compound No. 1 | | | | | | | | | | | |
| Methyl 2-nitro-5-(2',4'-dichlorophenoxy)thiobenzoate | 0.015% | 20.00% | 1333.333 | 8 | 0.0375% | 20.000% | 533.333 | 5 | 9.00% | 276.0 | 5 |
| Comparative prior compound | | | | | | | | | | | |
| Methyl 2-nitro-5-(2',4',6-trichlorophenoxy)thiobenzoate | 0.06 | 10.00 | 166.667 | 1 | 0.0925 | 10.000 | 108.12 | 1 | 5.25 | 57.6 | 1 |

Symbol
A : Concentration for withering wild radish
B : Concentration for withering wheat
B/A : Selective herbicidal coefficient between wild radish and wheat
A' : Average of concentration for withering broad-leaved weeds (speedwell, smallflower galinsoga, wild radish and kidney bean)
B/A' : Selective herbicidal coefficient between wheat and broad-leaved weeds
B' : Average of concentration for withering rice, wheat and corn
B'/A' : Selective herbicidal coefficient between wheat, rice and corn, and broad-leaved weeds (speedwell, smallflower galinsoga, wild radish and kidney bean)

Herbicidal effects of the compounds used in the present invention to various kinds of weed are illustrated in the following tests:

In following tests the numbers on tables indicate degree of injury to crops and weeds.

| Number | Degree of injury (%) | Overall condition of crops and weeds |
|--------|----------------------|--------------------------------------|
| 5 | 100 % | withering |
| 4 | 80 % | extreme |
| 3 | 60 % | moderate |
| 2 | 40 % | minor |
| 1 | 20 % | slight |
| 0 | 0 % | non injury |

TEST 2 (FOLIAGE TREATMENT TEST)

Seeds of wild radish (*Raphanus raphanistrum L.*) and wheat (*Triticum aestivum L.*) are individually seeded in clay pots packed with upland field soil in an amount sufficient to cover the seeds. After germination of the seeds, an aqueous suspension of wettable powder containing test compound mentioned below in the specified concentration and bentonite is sprayed onto the leaves at individually proper stages of seedling development. 15 days after spraying, injury to growth of the individual plants is rated. The results are shown in the following table.

Wheat: second – third true leaf
Wild radish: first – second true leaf

Table 2

| Compound No. | Concentration (PPM) | Degree of injury to test plants | |
|---|---|---|---|
| | | wild radish | wheat |
| 1 | 1000 | 5 | 1 – 2 |
| | 300 | 5 | 0 |
| | 100 | 5 | 0 |
| | 30 | 5 | 0 |
| | 10 | 3 – 5 | 0 |
| 2 | 1000 | 5 | 2 |
| | 300 | 5 | 1 |
| | 100 | 5 | 0 |
| | 30 | 5 | 0 |
| | 10 | 3 – 4 | 0 |
| 3 | 1000 | 5 | 1 – 2 |
| | 300 | 5 | 1 |
| | 100 | 5 | 0 |
| | 30 | 5 | 0 |
| | 10 | 2 – 3 | 0 |
| 4 | 1000 | 5 | 2 |
| | 300 | 5 | 0 |
| | 100 | 5 | 0 |
| | 30 | 2 | 0 |
| | 10 | 0 | 0 |

TEST 3 (FOLIAGE TREATMENT TEST)

Weeds mentioned below are tested in substantially the same manner as described in Test 2 and the following results are obtained:

Test plant

| Nipplewort | (*Jrigonotis peduncularis* [Trevir.]Benth.) : A |
| Ladysthumb | (*Polygonum Persicaria L.*) : B |
| Dock | (*Rumex japonica Houttuyn*) : C |
| Speedwell | (*Veronica didyma Tenore* var. *lilacina Yamazaki*) :D |
| Catchweed bedstraw | (*Galium aparine L.*) :E |
| Shepherdspurse | (*Capsella Bursa-patoris Medicus*) : F |
| Kiurigusa(Japanese name) | (*Trigonotis peduncularis Benth.*) : G |
| Common lambsquarters | (*Chenopodium album L.*) : H |

Stage

Nipplewort: second true leaf
Ladysthumb: first – second true leaf
Dock: seed leaf
Speedwell: second true leaf
Catchweed bedstraw: seed leaf
Shepherdspurse: third true leaf
Kiurigusa (Japanese name): second true leaf
Common lambsquarters: third true leaf Table 3

| Concentration of the Compound 1 (PPM) | Degree of injury to test plants | | | | | | | |
|---|---|---|---|---|---|---|---|---|
| | A | B | C | D | E | F | G | H |
| 100 | 5 | 5 | 5 | 5 | 5 | 5 | 5 | 5 |
| 30 | 5 | 5 | 5 | 5 | 5 | 5 | 5 | 5 |
| 10 | 4 | 5 | 5 | 4 | 3 | 4 | 4 | 5 |

TEST 4 (FOLIAGE TREATMENT TEST)

Crops and weeds mentioned below are tested by substantially the same manner as described in Test 2. 14 days after spraying, degree of injury to plants is observed. The following results are obtained:

Symbol

Weat (*Triticum aestivum L.*): A
Barley (*Hordeum vulgare L.*): B
Carrot (*Daucus Carota L.*): C
Beet (*Beta vulgaris L.* var. rapa DUMORT): D
Cucumber (*Cucumis sativa L.*): E
Wild radish(*Raphanus raphanistrum L.*): F
Soybean (*Glycine Max* MERR.): G
Spinach (*Spinacia oleracea L.*): H
Rice (*Oryza sativa L.*): I Table 4

| Concentration of the Compound No. 1 (PPM) | Degree of injury to test plants | | | | | | | | |
|---|---|---|---|---|---|---|---|---|---|
| | A | B | C | D | E | F | G | H | I |
| 1000 | 2 | 3 | 5 | 5 | 5 | 5 | 5 | 5 | 3 |
| 300 | 1.5 | 2 | 4 | 5 | 5 | 4 | 5 | 5 | 2 |
| 100 | 0 | 0 | 2 | 5 | 5 | 5 | 3 | 5 | 2 |
| 30 | 0 | 0 | 2 | 5 | 4 | 5 | 2 | 5 | 0 |
| 10 | 0 | 0 | 0 | 5 | 3 | 4.5 | 1 | 4.5 | 0 |

TEST 5 (SOIL TREATMENT TEST)

Clay pots are packed with upland field soil (volcanic soil) containing seeds of various kinds of weeds and then the surface of the soil in each pot is individually treated with an aqueous suspension of wettable powder containing test compounds described below in the specified concentration with bentonite. 60 days after the treatment, the degree of injury to test plants is observed and the following results are obtained: The plants are tabled using the following.

Cerastium (*Caespitosum Gilib*): A
Catchweed bedstrow (*Galium aparine L.*): B
Kiurigusa(Japanese name) (*Trigonotis peduncularis Benth*): C
Field cress (*Rorippa palustris Bess*): D
Pearlwont (*Gaginajaponica Ohwi*): E Eclipta (*Eclipta alba Hassks*): F Table 5

| Compound No. | Concentration (g/10a) | Degree of injury to test plants | | | | | |
|---|---|---|---|---|---|---|---|
| | | A | B | C | D | E | F |
| 1 | 200 | 5 | 5 | 5 | 5 | 5 | 5 |
| | 100 | 5 | 5 | 5 | 5 | 5 | 5 |
| | 50 | 4 | 4 | 4 | 4 | 4 | 4 |
| | 25 | 3 | 3 | 3 | 3 | 3 | 3 |
| 2 | 200 | 5 | 5 | 5 | 5 | 5 | 5 |
| | 100 | 5 | 5 | 5 | 5 | 5 | 5 |
| | 50 | 4 | 4 | 4 | 4 | 4 | 4 |
| | 25 | 3 | 3 | 3 | 3 | 3 | 3 |

TEST 6 (SOIL TREATMENT TEST)

Crops and weeds mentioned below are tested in substantially the same manner as described in Test 5. 60 days after the treatment, the degree of injury to the test plants is observed and the following results are obtained.

Wheat (*Triticum aesticum L.*): A
Wild radish (*Raphanus raphanistrum L.*): B
Carrot (*Daucus Carota L.*): C
Sawa-millet (*Panicum crus-galli L.*): D Table 6

| Compound No. | Concentration | Degree of injury to test plants | | | |
|---|---|---|---|---|---|
| | | A | B | C | D |
| 1 | 800 g/ 10 a | 0 | 5 | 5 | 5 |
| 2 | 800 g/ 10 a | 0 | 5 | 5 | 5 |

TEST 7 (FIELD TEST)

Seeds of wheat (*Triticum aestivum L.*) and wild radish (*Raphanus raphanistrum L.*) are individually seeded in field early in October. After germination of the seeds, an aqueous suspension of wettable powder containing compound No. 1 in the specified concentration with bentonite is sprayed onto the leaves at individually proper stages of seedling development. The degree of injury to the test plant and time of application are as set forth below:

Wheat: third – fourth true leaf
Wild radish: first – second true leaf

Table 7

| Concentration of the compound No. 1 (ppm) | Degree of injury to test plants | | | |
|---|---|---|---|---|
| | Nov.11 | | Dec.10 | |
| | wheat | wild radish | wheat | wild radish |
| 25 | 0 | 2 | 0 | 1 |
| 50 | 0 | 3.5 | 0 | 2.5 |
| 100 | 0 | 4.5 | 0 | 4 |
| 250 | 0 | 5 | 0 | 5 |
| 500 | 0 | 5 | 0 | 5 |
| 750 | 1 | 5 | 0 | 5 |
| 1000 | 1.5 | 5 | 0 | 5 |
| 2500 | 2 | 5 | 0 | 5 |
| 5000 | 2 | 5 | 0 | 5 |
| 10000 | 2.5 | 5 | 1 | 5 |

TEST 8 (SUBMERGED WATER TREATMENT)

Test Plant

Rice: *Oryza sativa L.*
Barnyard grass: *Echinochloa crusgalli*
Waterwort: *Elatine triandra* SCHK
False pimpernel: *Lindernia Pyxidaria* LINN
Pickerel-weed: *Monochoria vaginalis* (BURM. fil.) PRESL
Arrowhead: *Sagittaria pygmaea* MIQ.
Needle spikerush: *Eleocharis acicularis* ROEM. et SCHULT Method Plastic pots (diameter of the pot: 15cm, depth: 10cm) are packed with paddy soil (diluvial volcanic ash soil). Seeding or transplanting of rice is individually conducted by using the following methods.

A method: Seeds of rice are directly placed in the soil.

B method: Rice seedlings are transplanted at 3–4 stage of their true leaf.

C method: Seeds of rice are seeded and fixed to the soil without transplanting.

Mixtures of seeds of annual broad-leaved weeds (waterwort, false pimpernel and pickerel-weed) are seeded to surface of the soil. Seedlings of perennial weeds (arrowhead and needle spikerush) are individually transplanted into the pots. Seeds of barnyard grass are seeded in the pots. Duck weed is floated on water at the growing stage. After seeding transplanting or floating as mentioned above, the plastic pots are individually submerged in water 3 cm in depth and then suspensions of wettable powder containing a test compound and bentonite in the specified concentration are added dropwise to the pots. 20 days after, the degree of injury to the test plants is observed and the following results are obtained.

Table 8

| Compound No. | Concentration (g/10a) | Rice | | | Degree of injury to test plants | | | | |
|---|---|---|---|---|---|---|---|---|---|
| | | A method | B method | C method | Barnyard grass | Annual broad-leaved weed | Needle spikerush | Duck weed | Arrowhead |
| 1 | 100 | 2 | 0 | 0 | 5 | 5 | 4 | 5 | 5 |
| | 50 | 0 | 0 | 0 | 5 | 5 | 4 | 5 | 5 |
| | 25 | 0 | 0 | 0 | 4.5 | 5 | 4 | 5 | 5 |
| | 12.5 | 0 | 0 | 0 | 3.5 | 5 | 2 | 3 | 3 |
| 2 | 100 | 2.5 | 0 | 0 | 5 | 5 | 4 | 5 | 5 |
| | 50 | 0 | 0 | 0 | 5 | 5 | 4 | 5 | 5 |
| | 25 | 0 | 0 | 0 | 5 | 5 | 4 | 5 | 5 |
| | 12.5 | 0 | 0 | 0 | 3.5 | 5 | 2.5 | 3 | 3 |

TEST 9 (SUBMERGED WATER TREATMENT)

Test Plant

Redstem (Ammannia multiflora ROXB): fifth – sixth stage of leaf

Rotala (Rotala indica(WILLD)KOEHNE): tenth – twelfth stage of leaf.

The tests are run in substantially the same manner as set forth in Test 8 with the following results:

Table 9

| Compound No. | Concentration (g/10a) | Degree of injury to test plants | |
|---|---|---|---|
| | | Redstem | Rotala |
| 1 | 400 | 5 | 5 |
| | 200 | 5 | 5 |
| | 100 | 5 | 5 |
| | 50 | 5 | 5 |
| | 25 | 4 | 4 |
| 2 | 400 | 5 | 5 |
| | 200 | 5 | 5 |
| | 100 | 5 | 5 |
| | 50 | 5 | 5 |
| | 25 | 4 | 4 |

TEST 10 (SUBMERGED WATER TREATMENT)

Test plant

Rice: *Oryza sativa* L.
Barnyard grass: *Echinochloa crusgalli*
Waterwort: *Elatine triandra* SCHK.
False pimpernel: *Lindernia Pysidaria* L.
Pickerel-weed: *Monochoria vaginalis* (BURM.fil.) PRESL
Needle spikerush: *Eleocharis acicularis* ROEM.et SCHULT
Duckweed: *Lemna paucicostata* HEGELM
False loosestrife: *Ludwigia prostrata* ROXB
Rotala: *Rotala indica* (WILLD) KOEHNE
Abunome (Japanese name): *Dopatrium junceum* (ROXB.) HAMILT
Azetougarasi (Japanese name): *Vandellia angustifolia* BENTH Tests are carried out in substantially the same manner as described in Test 8, but the degree of injury to the test plants is observed 17 days after the treatment.

Table 10

| Compound No. | Concentration (g/10a) | Rice Transplanting | Degree of injury to test plants | | | |
|---|---|---|---|---|---|---|
| | | | Barnyard grass | Annual broad-leaved weeds* | Needle spikerush | Duck weed |
| 3 | 500 | 0 | 5 | 5 | 5 | 5 |
| | 250 | 0 | 5 | 5 | 5 | 5 |
| | 125 | 0 | 5 | 5 | 5 | 5 |
| | 62.5 | 0 | 5 | 5 | 5 | 5 |
| | 31.25 | 0 | 4 | 4 | 2 | 3 |
| | 16 | 0 | 2 | 2 | 0 | 0 |
| 4 | 500 | 0 | 5 | 5 | 5 | 5 |
| | 250 | 0 | 5 | 5 | 5 | 5 |
| | 125 | 0 | 5 | 5 | 5 | 5 |
| | 62.5 | 0 | 5 | 5 | 5 | 5 |
| | 31.25 | 0 | 5 | 5 | 5 | 5 |
| | 16 | 0 | 2 | 3 | 2 | 3 |

*Annual broad-leaved weeds mean mixtures of waterwort, false pimpernel, pickerel-weed, rotala, false loosestrife, abunome and azetougarasi.

PREPARATION OF COMPOSITIONS

Practical and preferred compositions are illustrated in the following examples wherein all parts are by weight.

EXAMPLE 1

| Methyl 2-nitro-5-(2′,4′-dichlorophenoxy) thiobenzoate | 20 parts |
| Talc | 80 parts |

The above materials were mixed ground and further mixed to give a dust.

EXAMPLE 2

| Ethyl 2-nitro-5-(2′,4′-dichlorophenoxy) thiobenzoate | 5 parts |
| Bentonite | 90 parts |
| Sodium lignin sulfonate | 5 parts |

The above materials were mixed and formed into granules.

EXAMPLE 3

| n-Propyl 2-nitro-5-(2′,4′-dichlorophenoxy) thiobenzoate | 10 parts |
| Bentonite | 87 parts |
| Sodium alkyl benzene sulfonate | 3 parts |

The above materials were mixed, ground and further mixed to give a wettable powder.

EXAMPLE 4

| Isopropyl 2-nitro-5-(2′,4′-dichlorophenoxy) thiobenzoate | 15 parts |
| Polyoxyethylene octhyl phenol ether | 5 parts |
| Xylene | 80 parts |

The above materials were mixed, and then water was added to the mixture to give an emulsion.

What is claimed is:

1. A compound of the formula:

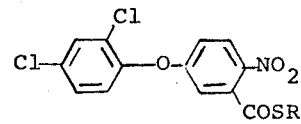

wherein R is lower alkyl.

2. The compound according to claim 1, in which R is methyl.

3. The compound according to claim 1, in which R is ethyl.

4. The compound according to claim 1, in which R is n-propyl.

5. The compound according to claim 1, in which R is isopropyl.

* * * * *